United States Patent
Shapiro (10) Patent No.: US 11,484,694 B2
(45) Date of Patent: Nov. 1, 2022

(54) MAGNETIC INJECTION OF THERAPEUTIC AGENTS BY ADDITION OF MATERIAL EXTRUSIONS WITH DIFFERING MAGNETIZATION AND MAGNETIC PERMEABILITY

(71) Applicant: OTOMAGNETICS, LLC, Rockville, MD (US)

(72) Inventor: Benjamin Shapiro, Washington, DC (US)

(73) Assignee: Otomagnetics, Inc., Gaithersburg, MD (US)

( * ) Notice: Subject to any disclaimer, the term of this patent is extended or adjusted under 35 U.S.C. 154(b) by 64 days.

(21) Appl. No.: 15/523,193

(22) PCT Filed: Oct. 30, 2015

(86) PCT No.: PCT/US2015/058205
§ 371 (c)(1),
(2) Date: Apr. 28, 2017

(87) PCT Pub. No.: WO2016/069982
PCT Pub. Date: May 6, 2016

(65) Prior Publication Data
US 2018/0280674 A1      Oct. 4, 2018

Related U.S. Application Data

(60) Provisional application No. 62/072,656, filed on Oct. 30, 2014.

(51) Int. Cl.
*A61M 37/00*     (2006.01)
*B82Y 5/00*      (2011.01)

(52) U.S. Cl.
CPC ............ *A61M 37/00* (2013.01); *B82Y 5/00* (2013.01)

(58) Field of Classification Search
CPC .... A61M 2037/0007; A61M 2205/057; A61M 37/00; A61M 2205/05; A61N 2/002;
(Continued)

(56) References Cited

U.S. PATENT DOCUMENTS 5,921,244 A * 7/1999 Chen .................. A61N 2/02
                                                   128/897
7,218,962 B2 * 5/2007 Freyman ............ A61M 37/00
                                                   600/13
(Continued)

FOREIGN PATENT DOCUMENTS

WO     2013026850 A1     2/2013
WO     2016069982 A1     5/2016

OTHER PUBLICATIONS

International Search Report and Written Opinion for International PCT Application No. PCT/US2015/058205, dated Jan. 27, 2016.

*Primary Examiner* — Kami A Bosworth
(74) *Attorney, Agent, or Firm* — K&L Gates LLP (57) ABSTRACT

A device and method for directing an agent that is magnetic or magnetizable having a magnetic configuration in which a first magnet has a first magnetization that is opposite to a second magnetization of the second magnet. The first magnet and the second magnet define a minimal convex set and the push node is outside the convex set. The first magnetic field and the second magnetic create a combined field and a pushing force.

14 Claims, 8 Drawing Sheets

(58) Field of Classification Search
CPC ... A61N 2/02; A61N 2/06; A61N 2/00; A61N 2/004; A61N 2/006; A61N 2/08; A61N 2/12; A61N 2/008
See application file for complete search history.

(56) References Cited

U.S. PATENT DOCUMENTS

| | | | |
|---|---|---|---|
| 8,544,474 B2 * | 10/2013 | Sandhu | A61K 9/5094 |
| | | | 128/897 |
| 2002/0147424 A1 * | 10/2002 | Ostrow | A61M 37/00 |
| | | | 604/20 |
| 2004/0143213 A1 * | 7/2004 | Hunter | A61M 37/00 |
| | | | 604/93.01 |
| 2005/0271732 A1 * | 12/2005 | Seeney | A61K 9/0009 |
| | | | 424/489 |
| 2006/0030816 A1 | 2/2006 | Zubry | |
| 2006/0228421 A1 * | 10/2006 | Seeney | A61N 2/12 |
| | | | 424/489 |
| 2007/0129693 A1 | 6/2007 | Hunter et al. | |
| 2009/0076324 A1 | 3/2009 | Takayama et al. | |
| 2010/0212676 A1 * | 8/2010 | Shapiro | A61M 37/0092 |
| | | | 128/899 |

* cited by examiner

MAGNETIC INJECTION OF THERAPEUTIC AGENTS BY ADDITION OF MATERIAL EXTRUSIONS WITH DIFFERING MAGNETIZATION AND MAGNETIC PERMEABILITY

CROSS-REFERENCE TO RELATED APPLICATIONS

This application is a national phase application of International Application No. PCT/US2015/058205, filed Oct. 30, 2015, which claims the benefit of priority on U.S. Provisional Application No. 62/072,656, filed Oct. 30, 2014, the content of which are both incorporated by reference.

TECHNICAL FIELD

This application relates generally to the field of therapeutic agent delivery, and more particularly to magnetic-assisted delivery of one or more therapeutic agents.

BACKGROUND

In conventional magnetic drug delivery, magnetically-responsive objects coated by or containing therapeutic agents can be injected systemically and then focused to targets in the body by applied magnetic fields. In such conventional magnetic therapy, an external magnet or magnets are typically placed outside the body and attract (pull in) magnetically responsive objects. For example, a magnet could be placed adjacent to a tumor and would attract magnetically-responsive objects, such as iron-oxide nanoparticles, to itself and thus concentrate them at the tumor location. This can become useful for treatment of cancer, stroke, infection, and other diseases because it allows therapy to be concentrated to disease sites (e.g., solid tumors, blood clots, infections) while keeping systemic concentrations low (thus minimizing side effects). The magnetically-responsive objects can be micro- or nano-scale iron oxide or other particles or objects, made and coated appropriately to be bio-compatible and therapeutically effective.

SUMMARY

The present disclosure provides improved devices, systems, and methods for magnetic agent delivery. In particular, it discloses devices, systems, and methods that can magnetically inject or push away magnetically-responsive objects such as iron-oxide nano-particles.

BRIEF DESCRIPTION OF THE DRAWINGS

Embodiments of devices, systems, and methods are illustrated in the figures of the accompanying drawings, which are meant to be exemplary and non-limiting, in which like references are intended to refer to like or corresponding parts, and in which.

DETAILED DESCRIPTION

Illustrative embodiments disclosed herein include devices, systems, and methods for directing an active agent to a target site. One operative principle for magnetically directing an agent (or therapeutics) associated with magnetic particles, which includes nano-particles, involves an arrangement of magnets. The magnets can have North (N) and South (S) poles that direct magnetic-particle formulations or agents from a container or a fluid/gel solution or cream or powder applied away from a target site (e.g. on a surface or in a cavity (e.g., an ear cavity) near the target site, or otherwise in the vicinity of target tissues) to the target site. Using this principle, the device, having a plurality of magnets or magnetic elements, can direct the agent from the container or fluid/gel solution or cream or powder to the target site. In one example, active agents, e.g. residing in magnetic or magnetically responsive particles, can be applied away from a target site (e.g., to skin on the body, on the surface of the eye, inside the ear canal) and the device can "push" or apply a force (F) on the particles, thereby directing the particles to the target site (T) (e.g., to a target under the skin, into the eye, into the middle or inner ear). In this example, the device can be used in combination with other aspects of medical technology, including medical nanotechnology. For instance, nanotechnology such as superparamagnetic, ferromagnetic, ferrimagnetic, or paramagnetic agents or particles may be used.

The device may include material additions, coverings or extrusions coupled to a base magnet or magnets. These additions, coverings, or extrusions could themselves be magnets or magnetic materials, or could have desirable magnetic properties such as low or high relative magnetic permeability. The magnets may be either permanent magnets or electro-magnets, or a combination of the two. The magnet may be used to induce a magnetization in the extrusions. The magnetism of the additions, coverings, or extrusions, or the induced magnetization of the extrusions, can act on the original magnetic field, generated by the base magnet, to deform it and create a push node or push region.

A push node or region is defined as a point or region of zero or lower magnetic field strength, which is surrounded by a non-zero or higher magnetic field strength. It is a confined region of minimal magnet field. For example, the magnets, material additions, coverings or extrusions may be so arranged that the magnetic field will cancel to a zero magnetic field at the push node, without cancelling around that point. Such a "cold spot" or local minimum of magnetic field strength can act to push away superparamagnetic, ferromagnetic, ferrimagnetic, or paramagnetic agents or particles, since those agents or particles will be attracted to the higher magnetic field outside the push node and will therefore experience outward forces away from the push node or push region.

The extrusions may be magnetic materials, permanent magnets or electromagnets, for example. Moreover, the extrusions may have a different magnetic relative permeability as compared to that of the magnet or magnets. This can cause the magnetic field of the device to deform, thereby creating a confined push node or region of low magnetic field strength. The push node or region enables the device to magnetically push or inject an agent or particle away from the device and towards a target site.

Generally, a magnetic field is greatest nearest the magnet from which it emanates, and then generally decreases. The device of the present disclosure, on the other hand, generates an overall deformed magnetic field that creates a local magnetic field "cold spot" (i.e., push node or region) near the device, around which the magnetic field increases. This increase of the magnetic field away (outwards) from the device can push away superparamagnetic, ferromagnetic, ferrimagnetic, or paramagnetic agents or particles.

Figure 1A:
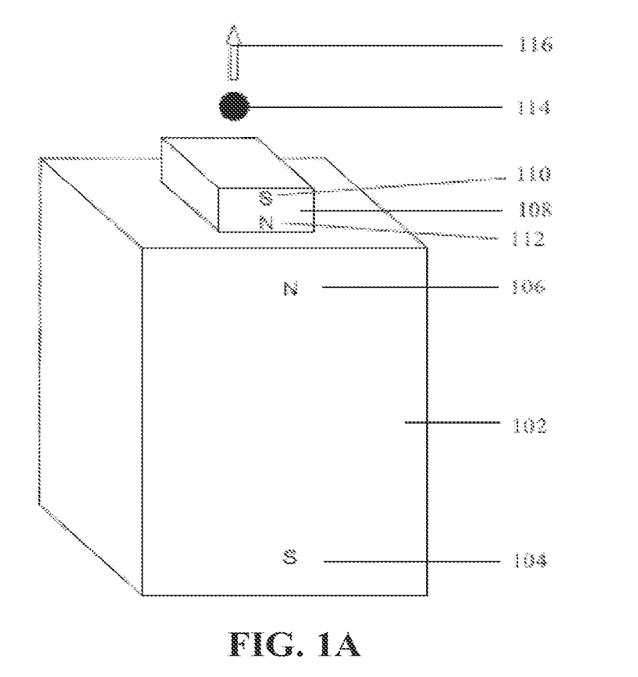
FIG. 1A illustrates an exemplary device for magnetic injection of an agent having a first (base) S→N rectangular magnet with a second smaller opposed rectangular N→S magnet attached to it.

FIG. 1A illustrates an exemplary device having a base magnet 102 (magnetized South 104 to North 106 in the upward direction) and a smaller opposed magnet 108 (magnetized South 110 to North 112 in the downward direction) that creates the push node 114 and the resulting push force 116 on magnetic or magnetizable agents. The agents or objects to be magnetically pushed may be superparamagnetic, ferromagnetic, ferrimagnetic, or paramagnetic agents or particles. The push node 114 is a confined region of minimal magnetic field above the device, and may be selected to have desired characteristics by manipulating the geometry, size, magnetization strength and orientation of the magnets, as detailed herein. The confined minimal magnetic field creates the push forces 116 for magnetically injecting an agent into a target site.

Numerical simulations of Maxwell's equations are detailed below to illustrate exemplary device configurations. In each simulation, a permanent magnet is used. However, some or all of the permanent magnet(s) may be replaced by an electromagnet(s) without significantly altering the devices performance or characteristics. Likewise, a device configuration may be selected that uses an electromagnet or electromagnets, or that uses modified shapes and configurations of added materials, to correct for any difference between permanent magnets and electromagnets, and that yields similar performance to that described herein. The shading in the figures indicates the strength of the magnetic field (dark for a high magnetic field strength, light for a zero or low magnetic field strength—hence the push node or push regions appear as white or light gray in FIGS. 1B, 6, 7 and 8). Black arrows denote the resulting forces on agents. These arrows are shown at the location of the push region, which is adjacent to the push node.

Figure 1B:
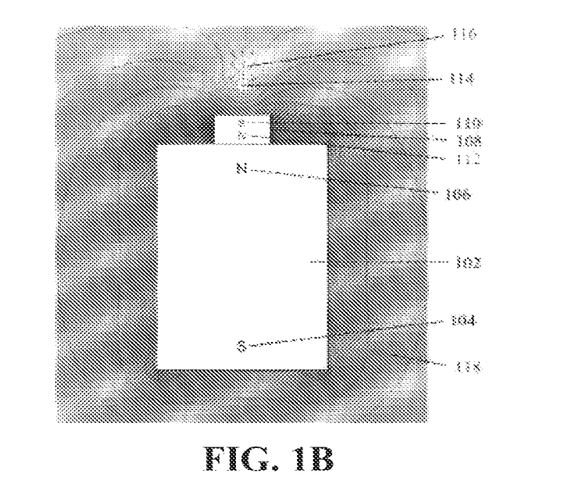
FIG. 1B illustrates the magnetic field created by the magnets of the device of FIG. 1A, the resulting magnetic push node, and the magnetic push forces that are produced.

FIG. 1B shows the magnetic field, push node, and magnetic push forces for an exemplary device of the type illustrated in FIG. 1A. This exemplary device is composed of two rectangular magnets, the base magnet 102 (magnetized South 104 to North 106 in the upward direction) and a smaller opposed magnet 108 (magnetized South 110 to North 112 in the downward direction) creates a magnetic field whose strength is denoted by the gray shading 118. Dark shading corresponds to a high magnetic field strength, light shading corresponds to a low or zero magnetic field strength. The disclosed inventive combination of magnets creates a magnetic field that has a confined magnetic field minimum (a push node 114) located outside (above) the device. The magnetic field strength increases outwards from this confined magnetic field minimum, creating outward push forces 116 on magnetic or magnetically responsive agents such as superparamagnetic, ferromagnetic, ferrimagnetic, or paramagnetic agents or particles.

The selection of the magnets size, geometry, and magnetization strength and orientation to achieve push outside the device is non-obvious, and an exemplary procedure to select device parameters to enable push is described herein below. From this procedure described below, and especially from the exemplary design space of FIG. 2, it will be clear that only a thin set of device parameters will achieve push, and these parameters must be selected appropriately as disclosed below herein. Once an effective push device design has been selected and disclosed, as in the present invention disclosure, then selection of additional designs or design modifications is achievable by someone who is knowledgeable in the art. For instance, if the size of all the magnets in the device is increased by a certain factor, for example all the magnets are made twice as large, the resulting design will also push effectively. Likewise, if the magnetization of all magnets is increased or decreased by a certain factor, for example all magnetizations are made twice as large, the device will also still push (and will push four times stronger since push is related to the square of the magnetization as detailed below). Further, if the magnetization orientation of each magnet is reversed, if North to South is changed to South to North for all magnets, then the magnets will remain in correct opposition to each other and will yield an equivalent device with equivalent push performance. Some or all of the permanent magnets may be replaced by electromagnets that provide an equivalent or similar magnetic field. A single magnet within the device may be replaced by two or more magnets that together act as the original magnet (for example one S→N magnet may be replaced by two adjacent magnets half its size with aligned [not opposed] magnetization S→N and S→N, which together will act the same as the original single magnet, as in FIG. 4). These and other modifications to the invention will be understood by someone familiar with the art of magnets and magnetism, do not change the essential features of the invention, and therefore fall under the scope of the current invention.

Figure 2:
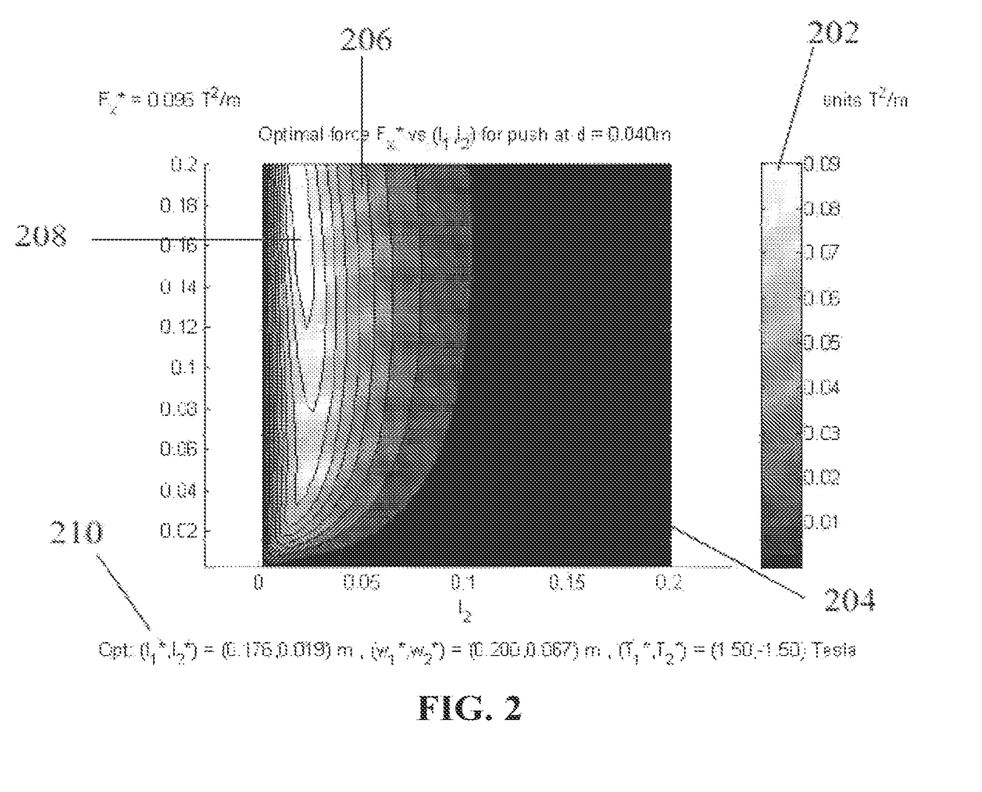
FIG. 2 illustrates selection of a device parameters that enable magnetic push. The push force $F_x$ is plotted against parameter choices of $l_1$ (1st magnet length) and $l_2$ (2nd magnet length) to enable selection of magnet sizes and magnet magnetization strengths and orientations to achieve push.

FIG. 2 illustrates selection of device parameters when implementing a two-magnet device according to the present disclosure. For a device composed of two rectangular magnets (as in FIG. 1A), nine (9) device parameters may be considered: six (6) magnet dimensions; two (2) magnetization strengths (including the polarity of magnetization of each magnet by their sign); and the distance between the device and the magnetic push region.

The dimensions and magnetization strength/direction of the magnets in the rectangular device shown in FIG. 1A may be selected based on the procedure disclosed below in order to achieve magnetic push. A similar procedure can be used for two magnets that have alternate shapes, for example a disc shape, or a truncated square or circular pyramid shape, or other shapes. Likewise, a similar design procedure can be applied to a system with 3 or more magnets or magnetic elements. The goal of the procedure is to select the parameters of the system (geometry and magnetization of the magnets) to achieve effective magnetic pushing. This selection procedure is non obvious and is described next for an exemplary rectangular two-magnet system of FIG. 1A.

Forces applied to magnetic (e.g., superparamagnetic, ferromagnetic, ferrimagnetic, or paramagnetic) particles or agents act from low to high magnetic field strengths. In other words, therapeutic agents are attracted towards regions of higher magnetic field strength and are repulsed away from regions of lower magnetic field strength. This is represented by the following equation known in the field of magnetic drug targeting:

$$F=k\nabla(H^2) \qquad \text{Equation 1}$$

F is the force on the agent;

k is a constant that depends on the size, shape, and properties of the agent (k is positive for superparamagnetic, ferromagnetic, ferrimagnetic, and paramagnetic agents);

$\nabla$ is a gradient operator in space; and

H is the applied magnetic field.

Bold typeface within Equation 1 denotes vectors. Moreover, the force F is given by the gradient of the magnetic field squared, and is therefore not necessarily in the same direction as the magnetic field H.

The spatial distribution of the magnetic field around magnets is described by Maxwell's equations (as, for example, in Fleisch, "A Students Guide to Maxwell's Equations"). For example, in FIG. 1A, magnetization of the base magnet represented by $T_1>0$ (positive) implies South to North is in the up direction in the base magnet, and magnetization of the second magnet $T_2<0$ (negative) implies South to North is in the down direction in the second magnet. The magnetic field created around a magnet is proportional to its magnetization, and the magnetization can further have an orientation. Accordingly, the magnetic field around magnet 1 may be represented as $T_1 H_1(x,y,z)$ and the magnetic field around magnet 2 may be represented as $T_2 H_2(x,y,z)$. Here $H_1$ and $H_2$ are the magnetic fields around each magnet (for each magnet's specific geometry and placement) when the magnet has been magnetized to exactly 1 Tesla. Since Maxwell's equations for the magnetic field are linear, and assuming that magnetization $T_1$ from one magnet does not substantially change (i.e., demagnetize) the magnetization $T_2$ of the other magnet, and vice versa, it is extrapolated that the magnetic field due to both magnets of the device is the sum of the magnetic field of each magnet individually. Deduced therefrom, the magnetic field at the desired push location (point p) may be represented as:

$$H(p)=T_1H_1(p)+T_2H_2(p) \qquad \text{Equation 2}$$

It follows from Equations 1 and 2 that the magnetic force (F) at location p is represented as:

$$F = k\nabla(H(p)^2) = k\nabla([T_1H_1(p) + T_2H_2(p)]^2) \qquad \text{Equation 3}$$
$$= k\{T_1^2 \nabla [H_1(p)]^2 + 2T_1T_2 \nabla [H_1(p) \cdot H_2(p)] + T_2^2 \nabla [H_2(p)]^2\}$$

These quantities $H_1(p)$ and $H_2(p)$ and their spatial derivatives can be readily computed by numerical methods (e.g., by software that computes magnetic fields) for any choice of magnet geometries ($l_1$, $w_1$, $h_1$, $l_2$, $w_2$, $h_2$). Alternatively, in some cases the quantities $H_1(p)$ and $H_2(p)$ can be calculated by analytical formulas, e.g., those provided in Engel-Herberta and Hesjedal, "Calculation of the Magnetic Stray Field of a Uniaxial Magnetic Domain", J. Appl. Phys. 97, 74504 (March 2005) for rectangular magnets, similar formulas exist for disc shaped magnets and other magnet shapes.

The component of the force along the device centerline can now be readily computed for any device geometry and magnet magnetizations strengths and orientations. For FIG. 1A, let z be the vertical axis, and set $$A=kd/dz[H_1(p)]^2, \; B=kd/dz[H_1(p) \cdot H_2(p)], \; C=kd/dz[H_2(p)]^2$$

then $$F_z=AT_1^2+2BT_1T_2+C\,T_2^2 \qquad \text{Equation 4}$$

and A, B, and C depend on the still-to-be-selected geometry of the device.

Using Equation 4, effective two-magnet push systems can be designed. It is beneficial for the device of the present disclosure to exhibit a positive $F_z$. To ensure a positive $F_z$ value is achieved, the signs of the A, B, C, $T_1$, and $T_2$ terms should be scrutinized. Since the strength of $H_z$ (i.e., the z-component of the magnetic field emanating from each magnet) decreases as distance from the magnet increases (because the magnetic field gets weaker further away from the magnet), A, B, C, which are formed from d/dz spatial derivatives of monotonically decreasing $H_z$'s, are always negative. Conversely, $T_1^2$ and $T_2^2$ are squares and are always positive.

A magnet's magnetization strength is established by the physics of the magnet's material makeup, and is limited by manufacturing, cost, and safety concerns. Permanent magnets used within the device of the present disclosure may exhibit magnetizations $T_1$ and $T_2$ in the ranges of, for example, $-1.5$ Tesla$\leq T_1 \leq +1.5$ Tesla and $-1.5$ Tesla$\leq T_2 \leq +1.5$ Tesla. (Electromagnets may exhibit greater magnetizations, but will also have a limit due to cost and safety concerns.) As these ranges demonstrate, $T_1$ and $T_2$ can be positive or negative, and their sign indicates the direction of magnetization (positive magnetization means magnetized up in FIG. 1A and negative magnetization means magnetized down in FIG. 1A). If a magnet's magnetization strength was unrestricted, devices could be designed to produce infinitely strong push forces. This is because the force scales with the strength (squared) of magnetization—doubling the magnetization of both magnets would quadruple the force, and infinitely strong magnetization would lead to infinitely strong push forces. Therefore, a properly maximized/optimized Equation 4 according to the present disclosure may be represented as:

$$F_x=AT_1^2+2BT_1T_2+CT_2^2$$

where $|T_1|\leq 1.5$Tesla, $|T_2|\leq 1.5$Tesla. $\qquad$ Equation 5 for permanent magnets. (For electromagnets the limits may be higher than 1.5 Tesla.)

It has been described that an absolute value of 1.5 Tesla is an example of a maximum allowable permanent magnet magnetization. However, one skilled in the art should appreciate that different situations (e.g. future advances in permanent magnet, electromagnet versus permanent magnet implementations) may lead to different realized maximum allowable magnetizations.

Using methods known in the field of optimization, specifically the method of Lagrange multipliers, or by taking the gradient of $F_z$ with respect to ($T_1$,$T_2$), it can be shown that the optimal selection of ($T_1$,$T_2$) can occur on the exemplary constraint boundary described herein (i.e., on $|T_1|=1.5$ Tesla and on $|T_2|=1.5$ Tesla). For example, setting $T_2=1.5$ Tesla makes $F_z$=A $T_1^2$+3B $T_1$+2.25 C in terms of $T_1$. This is a standard quadratic equation and the value that maximizes $F_z$ is therefore $T_1^*=-3B/2A$. If this value (i.e., $-3B/2A$) is outside $|T_1|<1.5$ Tesla, then the value closest to $-3B/2A$ is the $T_1^*$ "optimal" value. Together, the $T_1^*$ just described and $T_2=1.5$ Tesla is one optimal choice of magnetization $(T_1, T_2)$.

Three additional optimal pairs can be attained by: setting $T_2=-1.5$ Tesla and computing a $T_1^*$; or by setting $T_1=+1.5$ Tesla and then to $-1.5$ Tesla and computing two more optimal $T_2^*$ values. Thus, there are at least four potential pairs $(T_1^*, T_2^*)$ to maximize the push force $F_z$. Once the four pairs are calculated, the best pair (i.e., the pair having the highest positive value of $F_z$) should be selected. For example, if A=1, B=0.5, and C=1, the optimal magnetization pair is $(T_1^*, T_2^*)=(-0.75, +1.5)$, which produces a positive push force of $F_z=1.6875$. If instead, for example, A=1, B=1, and C=1, then no calculated $(T_1, T_2)$ pair produces a positive force. Therefore, device geometries exist that may exhibit magnetic pushing forces (first case) or that can only exhibit magnetic pulling forces (second case). A key inventive feature disclosed here is selection of magnet designs that enable effective pushing.

To select beneficial device geometries, the distance d from the device to the center of the push region, should be selected and then fixed. For example, for magnetically pushing therapeutics into ear compartments of adults, a distance d=4 cm=0.04 m may be beneficial, because this is the anticipated distance from a device held external to the head to the cochlea in adult patients, and is therefore the distance over which push would have to occur to magnetically inject therapy into the cochlea.

It may also be beneficial for the device to be symmetric in the x and y horizontal axes. For implementing such a symmetric device, the following can be assumed: $h_1=w_1$ and $h_2=w_2$. Having a set d, and knowing how to choose an optimal $(T_1^*, T_2^*)$ pair as described above, the remaining 4 parameters $(l_1, w_1, l_2, w_2)$ are determinable. In other words, the length and width of the two magnets that enable effective and maximal magnetic push are determinable.

One illustrative procedure to select these remaining design parameters involves numerically searching the 4 dimensional parameter space $(l_1, w_1, l_2, w_2)$ of a symmetric device. For any $(l_1, w_1, l_2, w_2)$, the coefficients A, B, C, can be computed by the analytical formulas in Engel-Herbert and Hesjedal ("Calculation of the Magnetic Stray Field of a Uniaxial Magnetic Domain", J. Appl. Phys. 97, 74504 (March 2005)). Once A,B,C are found for any choice of $(l_1, w_1, l_2, w_2)$, then $(T_1^*, T_2^*)$ may be chosen by the $(T_1^*, T_2^*)$ selection processes described above. Hence for each $(l_1, w_1, l_2, w_2)$ this yields a maximal push force design. To select the optimal (maximum force) $(l_1, w_1, l_2, w_2)$ parameters, an exemplary procedure is therefore to first select a minimum and maximum magnet width and magnet length. Then to select an $(l_1, l_2)$ pair and then for all $(w_1, w_2)$ pairs on a grid to compute $(T_1^*, T_2^*)$ and the resulting force $F_z$ and then select the pair $(w_1^*, w_2^*)$ that achieved the highest force $F_z^*$.

The results of such an exemplary optimization device design procedure are shown in FIG. 2. This figure shows the strength of the push force $F_z$ versus possible choices of $l_1$ and $l_2$ (the length of magnet 102 and the length magnet 108). For each pair $(l_1, l_2)$, the optimal $(w_1^*, w_2^*, T_1^*, T_2^*)$, the magnet widths and magnetizations, have already been selected, according to the method disclosed above. Shading 202 denotes the degree of magnetic push. Dark shading denotes ineffective designs where there is no magnetic push (illustrated as 204), or the magnetic push is negligible (illustrated as 206). The thin white region at the top left, which corresponds to a large first (base) magnet 102 with a small second magnet 108, is the only region that yields effective push (illustrated as 208). The detailed specifications for a magnet design in this white 'push-is-possible' region is provided at the bottom of the figure (illustrated as 210). For this exemplary design, which is also illustrated in FIG. 1B, the second magnet 108 has a specific smaller size as compared to the base magnet 102, and has an opposing magnetization (as indicated by $T_1^*$ and $T_2^*$ having opposite signs at the bottom of FIG. 2).

Optimization to select device design can include the use numerical, semi-numerical, and analytic approaches that are equivalent to the approach(es) described herein. The equations presented above can be optimized by other methods than those described. For example, the equations may be optimized by numerical approaches such as gradient descent, quadratic optimization, branch and bound, neural networks, genetic algorithms, and other methods known in the art. It should also be appreciated that the equations disclosed herein may be modified to account for related, different, or additional factors, such as for magnetic saturation, for electromagnets, for solid or air cores in the electromagnets, or for superparamagnetic, ferromagnetic, ferrimagnetic, or paramagnetic agents of other shapes than those described.

The design space illustrated in FIG. 2 indicates that only a small fraction of designs can achieve magnetic push, and the selection of magnet sizes and magnetizations enable an effective push.

Once one or a few effective magnet push designs have been disclosed, as in this disclosure, then an individual who is knowledgeable in the art may intuit other similar or equivalent designs that will also achieve magnetic push. For example, he or she may replace one magnet with two equivalent half-sized magnets oriented South to North in the same direction as a single magnet, or he or she may replace a small strong opposed magnet with a slightly larger less strong magnet, or he or she may scale the whole system to be larger or smaller, or he or she could select magnets of similar size, or he or she could flip the magnetization direction of both magnets in a two magnet design (S to N and then N to S could be changed to N to S and then S to N, which is an equivalent design because it is the opposition that leads to magnetic push). Such and other modifications retain the essential features of the current invention, and would fall under the scope of this disclosure. Further, in addition to the exemplary optimization and design method disclosed above, other analytical or numerical procedures of optimization known to those skilled in the art may also be used, such as gradient descent, branch and bound, neural networks, genetic algorithms etc. to select magnet push designs. Use of additional or different selection, design, or optimization techniques retains the above disclosed inventive features and falls under the scope of the current disclosure.

Figure 3:
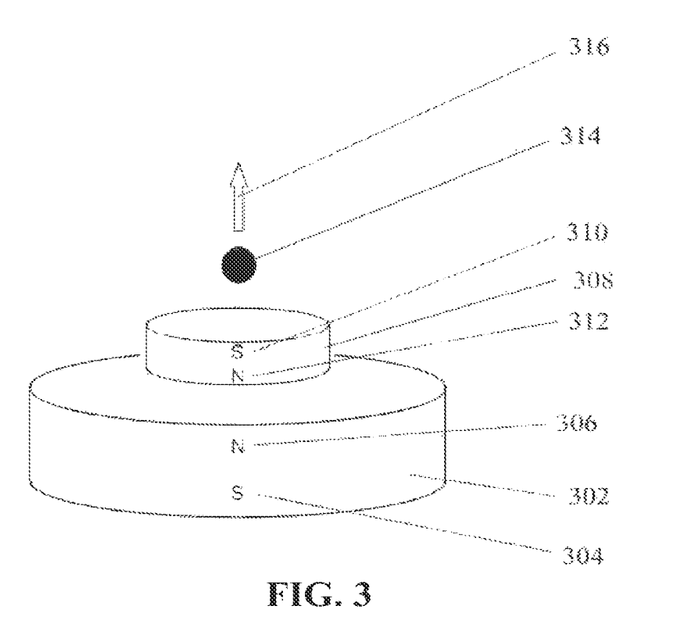
FIG. 3 illustrated a second exemplary push device composed of two opposed disc magnets.

Attention is now given to FIG. 3, which shows an alternate exemplary push device. Here the magnets are disc shaped, rather than rectangular as in FIG. 1A. The first (base) magnet 302 is magnetized South 304 to North 306 in the upwards direction. The second smaller disc magnet 308 is magnetized South 310 to North 312 in the downwards direction. This arrangement and magnetization of magnets, when geometry and magnetization strength is appropriately selected using method such as disclosed above, can create a push node 314 outside and above the device. This push node can then create push forces 316 on superparamagnetic, ferromagnetic, ferrimagnetic, or paramagnetic agents or particles.

Figure 4:
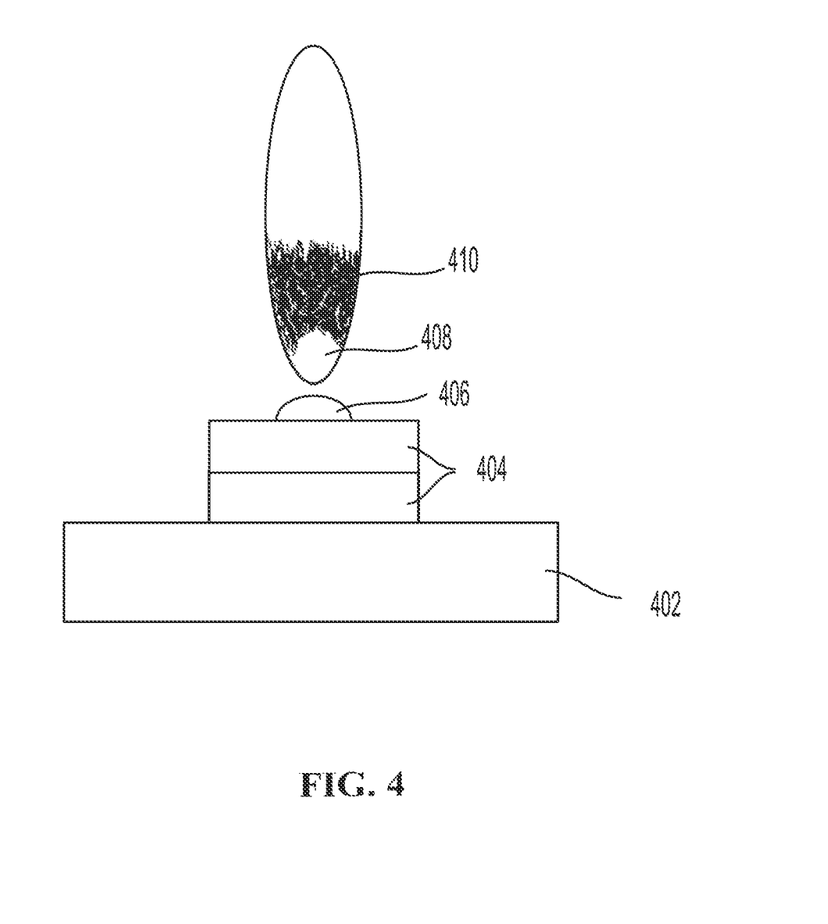
FIG. 4 shows experimental demonstration of a third exemplary device composed of three disc magnets, illustrates the presence of the magnetic push node and pushing of magnetically responsive particles against the force of gravity.

FIG. 4 shows an exemplary experimental embodiment. This disc magnet exemplary device was designed, and its geometry and magnetizations were selected, using a similar procedure as detailed above for rectangular magnets. The base disc magnet 402 is magnetized with South to North in the up direction. Above it, the opposing two disc magnets 404 are magnetized in the opposite South to North down direction. A brass screw 406 is inserted through the center of all 3 disc magnets and holds the assembly together. The strength and size of the magnets has been carefully selected, using the methods disclosed above and as illustrated in FIG. 2, to create a push node located above the device. This push node 408 magnetically pushes magnetically responsive (iron) particles 410 up and levitates them against gravity.

Figure 5:
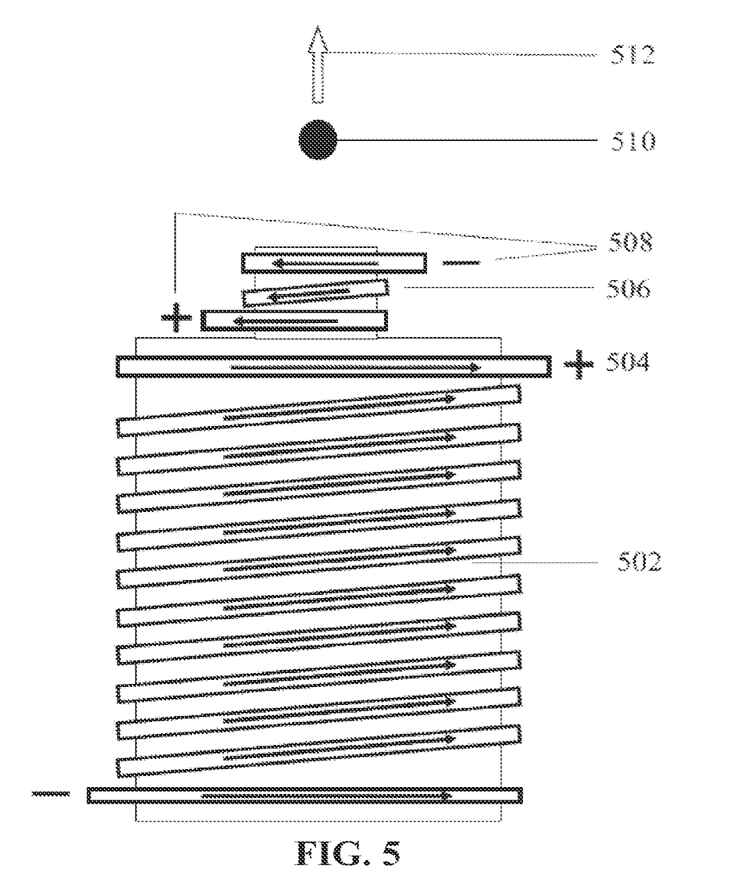
FIG. 5 illustrates a fourth exemplary embodiment where the opposed magnets are electromagnets.

As previously noted, in alternate embodiments some or all of the permanent magnets may be replaced by electromagnets. FIG. 5 illustrates an exemplary device design that is essentially equivalent to the design shown in FIG. 1A except that the permanent magnets have been replaced by electromagnets. The first (base) magnet 502 is now an electromagnet with clockwise current (left to right in the figure, illustrated as 504). In opposition, the smaller second magnet 506 has a counterclockwise current (right to left, illustrated as 508). The two counter currents will create opposed magnetizations for the two magnets. Selecting the size of the magnets, and the strength of the currents, using procedures essentially similar to those detailed above, can create a push node or region 510 (a location of confined minimal magnetic field strength) above and outside the system. As for the permanent magnet device shown in FIGS. 1A and 1B, this will create a push force 512 on superparamagnetic, ferromagnetic, ferrimagnetic, or paramagnetic agents or particles. Also as for permanent magnets, if the orientation of all the electromagnets is reversed, they will remain in the same opposition to each other, and their overall push performance would remain unchanged. One knowledgeable in the art of magnets and magnetism will further recognize that electromagnets may be constructed with different types of coil windings, with or without air or solid cores, with or without cooling, and that these different electromagnet implementations do not change the essential features of the current disclosure and so continue to fall under the scope of the present invention.

Attention is now given to elements of device construction. Opposing magnets, such as disclosed above, will typically have forces between them that will tend to push them apart, but magnets can be bonded together by a variety of means known in the art. Two (or more) opposing magnets may be held together by glue, epoxy, or adhesive. To provide additional strength, two or more magnets or magnetic elements may also be fully or partially surrounded by a coating or band of another material, such as by a coating of epoxy around the whole device or by a band of plastic, rubber, metal (magnetic or non-magnetic), or other material that will act or further act to keep the magnets or magnetic materials together. Magnets can be attached to each other using zipties, by screws and nuts (magnetic or non-magnetic), and by being put inside appropriately shaped holders, for example by being inserted into strong plastic holders manufactured by any of a variety of methods (plastic molding, 3D printing, etc). For suitable magnet materials, magnets may also be soldered together, for example by braze bonding (Houska, U.S. Pat. No. 3,923,232). Other methods are known in the art for securely attaching magnets together, and using such other methods to attach the magnets together will not change the underlying inventive aspect, and therefore still falls under the scope of the current invention. For electromagnets, two or more electromagnets may be secured together by external housing, by a shared solid core or by solid cores attached to each other, or by other means known in the art.

Figure 6:
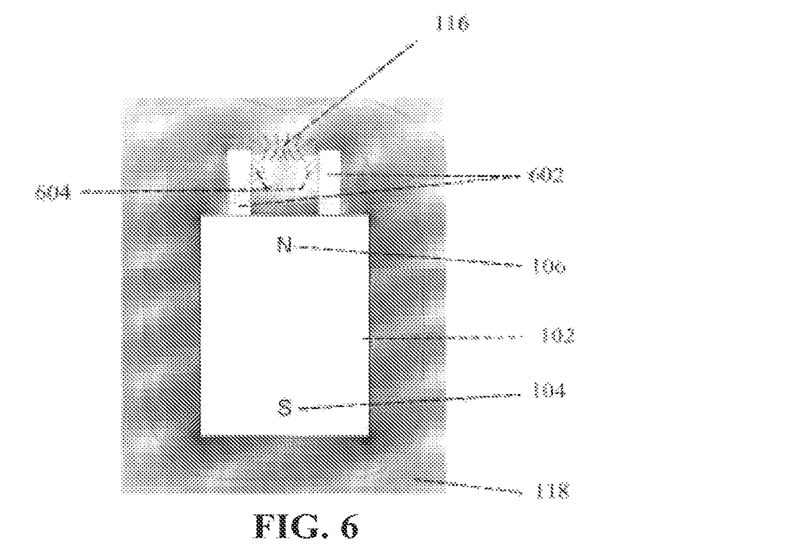
FIG. 6 illustrates a fifth exemplary device for magnetic injection of an agent having two elongated extrusions made of high mu material.
Figure 7:
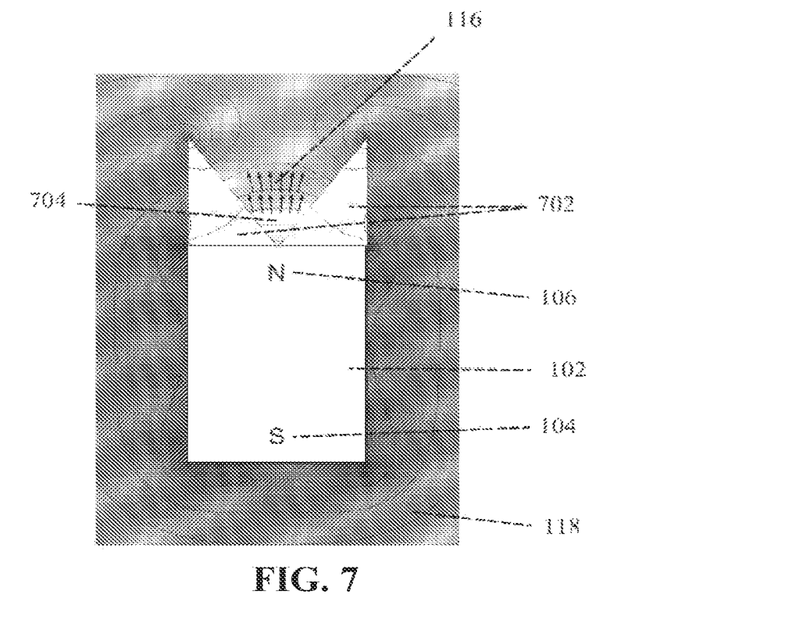
FIG. 7 illustrates a sixth exemplary device for magnetic injection of an agent having two triangular extrusions made of high mu material.
Figure 8:
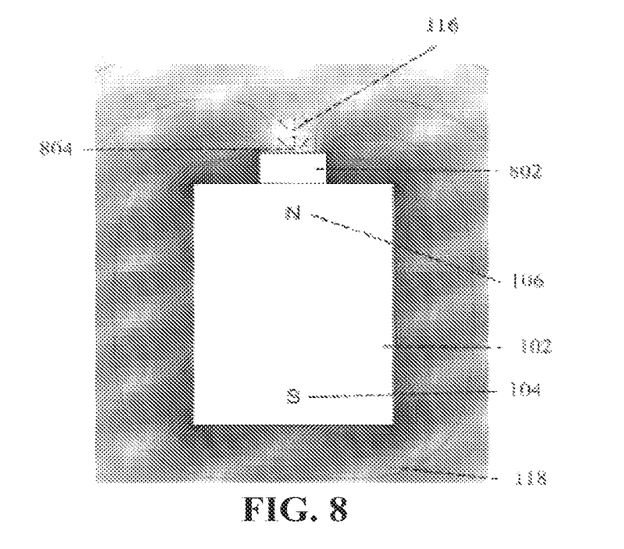
FIG. 8 illustrates the device for magnetic injection of an agent having an extrusion made of superconducting material.

Attention is now given to additional exemplary devices composed of base magnets with added material extrusions that can achieve a push force. FIGS. 6 through 8 illustrate devices configured to generate magnetic push forces. The devices include a first base magnet or magnetic element 102 and one or more extrusions 602, 702, 802 coupled to the magnet or magnetic element. While the device is illustrated and described as having one base magnet or magnetic element 102, it should be appreciated that the device may include more than one base magnet or magnetic element. The base magnet or magnetic element 102 may be a permanent magnet or an electromagnet. The extrusion(s) 602, 702, 802 may be made of the same material, or each extrusion may be made of a different material.

FIG. 6 illustrates the addition of two high mu material extrusions 602. A high mu material, as used herein, is a material that has a high relative magnetic permeability ($\mu_r$). For example, magnetic alloy (mumetal) materials can have $\mu_r > 80,000$. In contrast, the magnetic permeability for permanent magnet materials is usually on the order of $\mu_r \approx 4,000$. Thus, high mu materials can have a magnetic permeability up to twenty (20) times greater than that of permanent magnets. The extrusions 602 change the distribution of the magnetic field (i.e., they may create magnetic field minimum node or nodes inside 604 or above the device). In the exemplary device of FIG. 6, two low magnetic field nodes 604 are created between the high mu extrusions 602. There is a bridge of low magnetic field between these two nodes 604, and magnetic push forces 116 emanate outwards from that bridge. This push force 116 extends above and outside the device.

The extrusions 602 may have square or elongated surface areas (as illustrated in FIG. 6). Alternatively, the extrusions 702 may have triangular shapes (illustrated in FIG. 7). The triangular extrusions 702 of FIG. 7 may create a push region 704 than the extrusions 602 illustrated in FIG. 6, with a resulting push force 116 between the two triangular extrusions. As illustrated in FIG. 8, the device may include an extrusion 802 made of superconducting material. Such a superconducting extrusion 802 may create a low magnetic field strength node or region above it 804 and resulting magnetic push forces above the node 116. When superconducting material is used, the device may need to be maintained below room temperature because present superconductors often experience performance degradation at and above room temperature.

It may be beneficial to have the device or system meet other necessary or advantageous constraints. For example, it may be desirable to have the device be less than a certain weight, be hand held, fit the shape of a hand for easy manipulation by a doctor or clinician, or have cavities or other open spaces made available within, around, or between the magnets for installation of a light or a small camera to provide visual guidance for a doctor or clinician. Someone skilled in the art would recognize that the exemplary devices and design procedures disclosed above can be readily modified to include consideration of such desirable features, and that the resulting devices, systems, and methods would continue to fall under the scope of the present invention.

Once presented with the above methods, a person skilled in the art of magnetism and magnetic materials would recognize that the illustrations in the figures are exemplary, and that there are other situations with magnets of different shape, different magnetism orientation (e.g. S→N instead of N→S, or magnetized sideways instead of top to bottom), different shapes of added materials, and different material properties, that would also be effective, and that thereby fall under the scope of this disclosure.

It is understood that the electromagnets can be used as or in conjunction with the magnets or magnetic elements. An electromagnet is a magnet that is powered with electricity. Unlike a permanent magnet, the strength of an electromagnet can easily be changed by changing the amount of electric current that flows through it. The poles of an electromagnet can even be reversed by reversing the flow of electricity.

If the agents associated with the magnetic or magnetizable superparamagnetic, ferromagnetic, ferrimagnetic, or paramagnetic agents or particles are cells, the cell may be any biologic cell that is itself capable of responding to a magnetic field, or can incorporate one or more magnetic particles or agents that can respond to a magnetic field. In this way, cells may also be pushed by the magnetic systems and devices disclosed herein. The cells used in connection with the present disclosure may be, for example, endothelial cells, or ectoderm-, mesoderm-, or endoderm-derived cells. Additionally, any stem or mature or immature cell originating from tissue or fluids (e.g. from blood) or from cell layers in animals or humans may be modified to be useful in connection with the present disclosure.

If the device is designed to be deployed to internal (in vivo) locations within a human or animal body, the outer surfaces of the device can be biocompatible. Any non-biocompatible materials within any such device may be contained within or covered by a biocompatible material that does not significantly limit or interfere with the magnetic fields. Biocompatible coatings for use in connection with devices of the present disclosure may include, e.g., various biocompatible polymers, metals, and other synthetic, natural, or biologic materials.

Figure 9A:
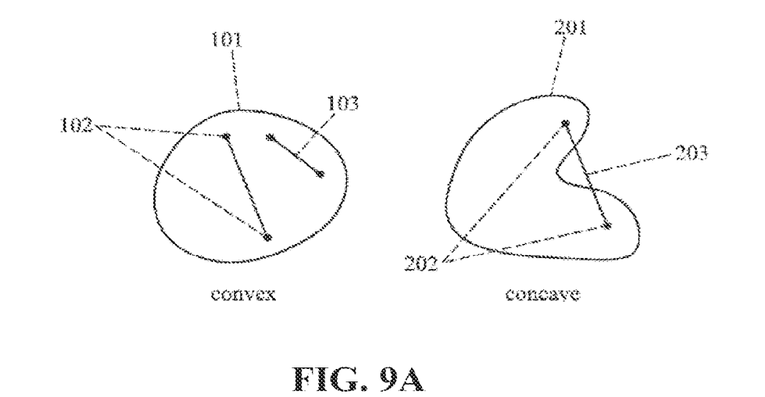
FIG. 9 illustrates a minimal convex set.
Figure 9B:
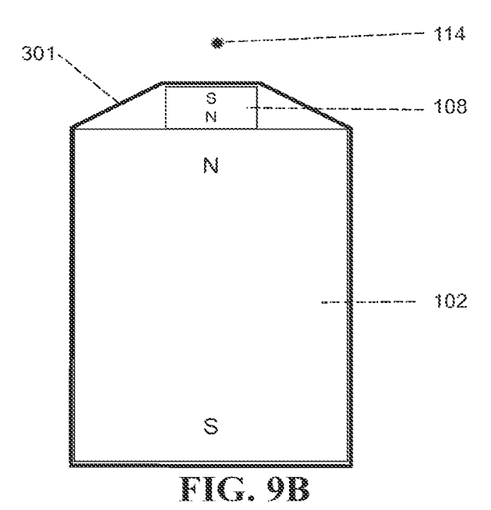
Figure 9C:
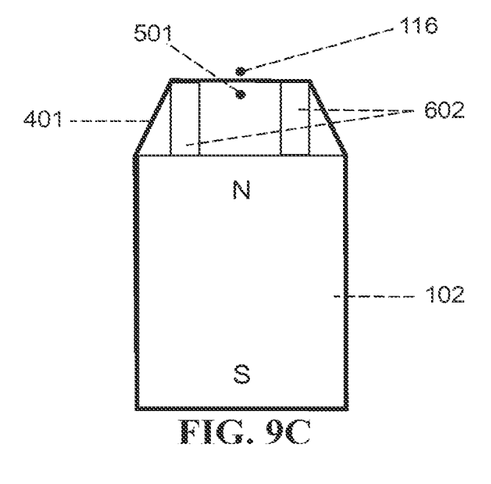

To avoid ambiguity, the term "outside" of a device is defined by the known concept of a minimal convex set. FIG. 9A illustrates a convex versus a non-convex shape. In a convex set or a convex shape 101, all straight lines 103 from any one point to any other point 102 of the shape 101 are themselves wholly within the shape 101. In a non-convex shape (for example in a concave shape, 201), at least a part of one of the straight lines 203 lies outside the shape. One source for the concept of the convex shape and a minimal convex shape is http://mathworld.wolfram.com/Convex-.html as of the filing date of this disclosure. There are multiple other standard sources, for example, the book "A Course in Convexity" by Alexander Barvinok, Graduate Studies in Mathematics, volume 54. The minimal convex shape singles out one particular convex shape out of many. To illustrate, attention is now given to FIGS. 9B and 9C which show the minimal convex set that encloses the magnets and magnetic materials of the exemplary devices previously shown in FIGS. 1B and 6. The minimal convex sets are the smallest convex shapes 301, 401 that wholly contain the magnets and magnetic materials. Outside a device is therefore defined as outside the minimal convex set that encloses all magnets and magnetic materials for that device. Hence in FIG. 9B, the push node 114 is outside the device. In FIG. 9C the push force location 116 is outside the device whereas the example point 501 is not outside the device. Therefore a push node outside the device is defined without ambiguity as outside the minimal convex shape that wholly encloses all the magnets and magnetic materials of that device.

The above detailed description, the examples illustrated therein, and the drawings are for illustrative purposes only and are not intended to limit the scope and spirit of the invention, and its equivalents, as defined by the appended claims. One skilled in the art will recognize that many variations can be made to the invention disclosed in this specification without departing from the scope and spirit of the invention.

What is claimed is:

1. A method for directing an agent into or through material, comprising:
    positioning a magnetic configuration having a plurality of magnetic elements, wherein a first magnetic element having a first magnetic north-south pole in the plurality of magnetic elements produces a first magnetic field;
    a second magnetic element having a second magnetic north-south pole in the plurality of magnetic elements produces a second magnetic field;
    the first magnetic element has a first magnetization that is opposite to a second magnetization of the second magnetic element;
    the first magnetic element and the second magnetic element are positioned in a linear orientation along a vertical axis such that the first magnetic north-south pole of the first magnetic element abuts to a same polarity of the second magnetic north-south pole of the second magnetic element and define a minimal convex set, and wherein a push node is outside the minimal convex set;
    the first magnetic field and the second magnetic field create a combined magnetic field and a pushing force from the first magnetic element and the second magnetic element, and the second magnetic field has a further spatial extent than the first magnetic field, wherein the pushing force is in a vertical direction along the vertical axis of the linear orientation of the first magnetic element and the second magnetic element; and
    moving the agent with the pushing force into or through the material.

2. The method as claimed in claim 1, wherein the agent is magnetic, superparamagnetic, ferrimagnetic, ferromagnetic, or paramagnetic.

3. The method as claimed in claim 1, further comprising depositing the agent onto the material or putting the agent into a cavity, a canal, and a compartment, wherein the material is tissue.

4. The method as claimed in claim 1, wherein the first magnetic element and the second magnetic element are bonded together.

5. The method as claimed in claim 1, wherein the second magnetic element comprises one magnet or multiple magnets aligned in the same north-south down direction to combine and create the second magnetic field.

6. The method of claim 1, wherein the first magnetic element comprises one or more of a permanent magnet or an electromagnet.

7. The method of claim 1, wherein the second magnetic element comprises an electromagnet, and wherein the second magnetization of the second magnetic element is manipulatable based on a desired push node force.

8. The method as claimed in claim 1, wherein either the first magnetic field or the second magnetic field has a field strength of about 1 micro-Tesla to about 10 Tesla.

9. A device for directing an agent that is magnetic or magnetizable, comprising:
- a magnetic configuration having a plurality of magnets, wherein a first magnetic element having a first magnetic north-south pole in the plurality of magnets produces a first magnetic field;
- a second magnetic element having a second magnetic north-south pole in the plurality of magnets produces a second magnetic field;
- the first magnetic element has a first magnetization that is opposite to a second magnetization of the second magnetic element;
- the first magnetic element and the second magnetic element are positioned in a linear orientation along a vertical axis such that the first magnetic north-south pole of the first magnetic element abuts to a same polarity of the second magnetic north-south pole of the second magnetic element and define a minimal convex set, and wherein a push node is outside the minimal convex set;
- the first magnetic field and the second magnetic field create a combined field and a pushing force from the first magnetic element and the second magnetic element, and the second magnetic field has a further spatial extent than the first magnetic field, wherein the pushing force is in a vertical direction along the vertical axis of the linear orientation of the first magnetic element and the second magnetic element.

10. The device as claimed in claim 9, wherein the combined field repels a magnetic, superparamagnetic, ferrimagnetic, ferromagnetic, or paramagnetic agent.

11. The device as claimed in claim 9, wherein the first magnetic element and the second magnetic element are bonded together.

12. The device as claimed in claim 9, wherein the first magnetic field or the second magnetic field has a field strength of about 1 micro-Tesla to about 10 Tesla.

13. The device as claimed in claim 9, wherein the first magnetic element or the second magnetic element is electromagnetic.

14. A device comprising a magnetic configuration having a magnetic element that produces a first magnetic field;
- a magnetizable material that interacts with the first magnetic field to produce a second magnetic field;
- the magnetic element and the magnetizable material are positioned in a linear orientation along a vertical axis such that a first magnetic north-south pole of the magnetic element abuts to a same polarity of a second magnetic north-south pole of the magnetizable material and define a minimal convex set, and wherein a push node is outside the minimal convex set; and
- the first magnetic field and the second magnetic create a combined field and a pushing force, wherein the magnetic element and the magnetizable material are opposite by pole to one another, wherein the pushing force is in a vertical direction along the vertical axis of the linear orientation of the magnetic element and the magnetizable material.

* * * * *